(12) United States Patent
De Greyt et al.

(10) Patent No.: US 8,178,326 B2
(45) Date of Patent: May 15, 2012

(54) PRODUCING ESTERS OF FATTY ACID AND C1-C3 ALKYL ALCOHOLS

(75) Inventors: Wim De Greyt, Sinaai (BE); Marc Kellens, Muizen (BE); Hans Christian Holm, Hellerup (DK); Morten Wurtz Christensen, Lyngby (DK); Per Munk Nielsen, Hilleroed (DK)

(73) Assignees: Novozymes A/S, Bagsvaerd (DK); N.V. Desmet Ballestra Group S.A., Zaventem (BE)

( * ) Notice: Subject to any disclaimer, the term of this patent is extended or adjusted under 35 U.S.C. 154(b) by 414 days.

(21) Appl. No.: 12/531,742

(22) PCT Filed: Apr. 9, 2008

(86) PCT No.: PCT/EP2008/054309
§ 371 (c)(1),
(2), (4) Date: Sep. 17, 2009

(87) PCT Pub. No.: WO2008/125574
PCT Pub. Date: Oct. 23, 2008

(65) Prior Publication Data
US 2010/0047884 A1 Feb. 25, 2010

Related U.S. Application Data

(60) Provisional application No. 60/913,325, filed on Apr. 23, 2007.

(30) Foreign Application Priority Data

Apr. 11, 2007 (EP) .................................... 07105944

(51) Int. Cl.
*C12P 7/62* (2006.01)

(52) U.S. Cl. ........ 435/135; 435/155; 435/134; 435/136; 435/137

(58) Field of Classification Search ........................ None
See application file for complete search history.

(56) References Cited

U.S. PATENT DOCUMENTS

| | | | |
|---|---|---|---|
| 2,588,435 | A | 3/1952 | Van Loon et al. |
| 4,164,506 | A | 8/1979 | Kawahara et al. |
| 6,822,105 | B1 | 11/2004 | Luxem et al. |
| 7,087,771 | B2 | 8/2006 | Luxem et al. |
| 2002/0197687 | A1 | 12/2002 | Brunner et al. |
| 2004/0186307 | A1 | 9/2004 | Piacentitn et al. |
| 2005/0233426 | A1 | 10/2005 | Schoerken et al. |

FOREIGN PATENT DOCUMENTS

| | | |
|---|---|---|
| EP | 1 324 818 | 10/2004 |
| EP | 1 270 734 | 12/2007 |

OTHER PUBLICATIONS

Pastor et al, Applied Biochemistry and Biotechnology vol. 50, pp. 251-263 (1995).
Sahoo et al, Fuel, vol. 86, pp. 448-454 (2007).
Watanabe et al, Journal of Molecular Catalysis B; Enzymatic, vol. 44, pp. 99-105 (2007).
"Corps Gras d'Origines Animale et Vegetale Determination de l'Indice d'Acide et de l'Acidite. Oanimal and Vegetable Fats and Oils—Determination of Acid Value and Acidity," Normes Francaises, Afnor, Paris, FR, Aug. 1, 1996.

*Primary Examiner* — Blaine Lankford, Jr.
(74) *Attorney, Agent, or Firm* — Kristina J. McNamara

(57) ABSTRACT

The invention relates to the utilization of fatty materials with substantial free fatty acid content in the production of biodiesel by the use of microbial enzymes that are effective in a solvent-free process for the production of esters of fatty acids and $C_1$-$C_3$ alkyl alcohols.

16 Claims, 1 Drawing Sheet

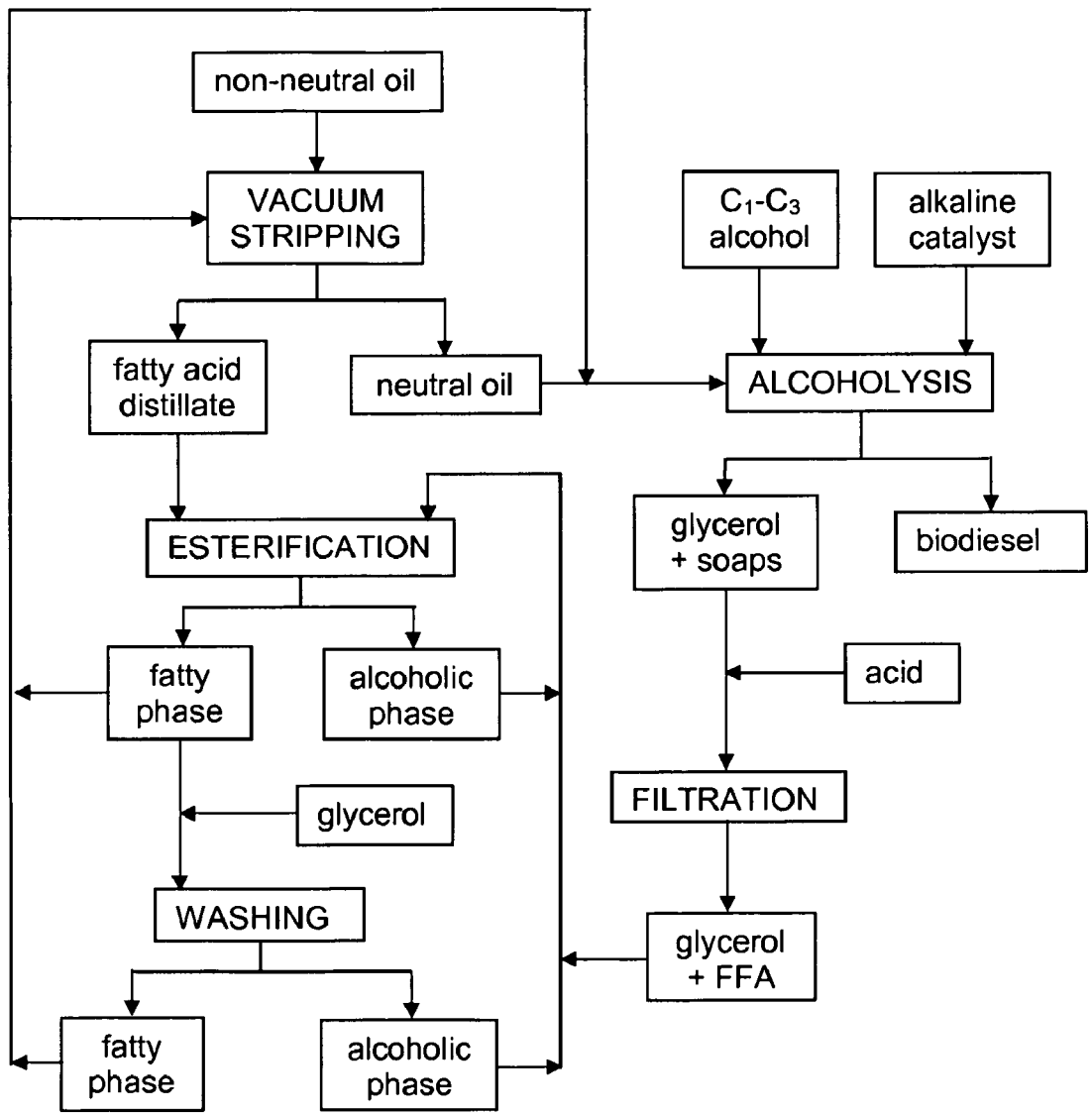

PRODUCING ESTERS OF FATTY ACID AND C1-C3 ALKYL ALCOHOLS

CROSS-REFERENCE TO RELATED APPLICATIONS

This application is a 35 U.S.C. 371 national application of PCT/EP2008/054309 filed Apr. 9, 2008, which claims priority or the benefit under 35 U.S.C. 119 of European application no. 07105944.8 filed Apr. 11, 2007 and U.S. provisional application No. 60/913,325 filed Apr. 23, 2007, the contents of which are fully incorporated herein by reference.

FIELD OF THE INVENTION

The invention relates to the utilisation of fatty materials with substantial free fatty acid content in the production of biodiesel.

BACKGROUND OF THE INVENTION

As a result of the increasing interest in renewable resources in general and biofuels in particular, a number of processes has been developed for the production of esters of fatty acids and lower alkyl alcohols, which esters are also referred to as 'biodiesel'. Early 'biodiesel' processes prescribed the use of neutral raw materials and thereby competed with food applications. Accordingly, there is an incentive to exploit cheaper alternative sources of fatty acid moieties as raw material for biodiesel production. This often means that such materials may contain free fatty acids and that their FFA contents can vary over a wide range.

Accordingly, U.S. Pat. No. 4,164,506 discloses a process comprising the esterification of free fatty acids of unrefined fats with a lower alcohol in an amount larger than its solubility in the fats in the presence of an acid catalyst. However, several lower alcohols have a boiling point that is lower than the boiling point of water which implies that it is impossible to remove the water formed by the esterification while retaining the lower alcohol in the reaction mixture. Shifting the esterification equilibrium to the ester side therefore requires the use of a large excess of lower alcohol.

This disadvantage can be overcome by using a high boiling alcohol such as glycerol as disclosed in U.S. Pat. No. 2,588,435. Using such high boiling alcohols has the additional advantage that the reaction can be carried out at a higher temperature, which increases the rate constant of the esterification reaction, without having to operate under superatmospheric pressure. In fact, as disclosed in U.S. Pat. No. 6,822,105, the esterification can now be carried out under vacuum, which promotes the evaporation of the water formed by the esterification reaction which is thereby shifted towards the ester side. The use of nitrogen during a vacuum stripping operation further facilitates the water evaporation.

However, as demonstrated by the examples in U.S. Pat. Nos. 6,822,105 and 7,087,771, the esterification reaction is quite slow and it can take some 7 to 11 hours before the acid value of the reaction mixture, which is indicative of the residual free fatty acid content, has decreased to a value below 0.4 (mg KOH per g oil), which in industrial practice is the maximum value for a starting material for a transesterification process leading to biodiesel. The example in US Patent Application Publication 2004/0186307 employing a solid esterification catalyst, which is present in a packed bed inside the esterification reactor, also mentions a reaction time of 5 hours at a temperature of 200° C. Holding fatty materials at such a high temperature for long periods of time can lead to the formation of unwanted side-products.

Accordingly, there is a strong preference for an esterification reaction at lower temperatures and for a catalyst that does not cause side-products to be formed. Operating a lower temperature can also lead to energy savings. In this context, the use of enzymes in general and of lipases in particular merits consideration. However, the use of enzymes is far from straightforward. Their activity depends on the water concentration but water also affects the position of the esterification equilibrium. Moreover, the reagents should be well mixed, which is why the literature often mentions the use of solvents, e.g. ref. Pastor, E.; Otero, C.; Ballesteros, A. 1994 Applied Biochemistry and Biotechnology Vol 50, p: 251-263: Synthesis of Mono- and Dioleylglycerols Using an Immobilized Lipase. For industrial processes the use of solvents raises the cost of operation and is therefore preferably avoided.

Accordingly, there is a clear need for an enzymatic process that allows fatty raw materials with variable free fatty acid contents to be utilised as raw material for biodiesel production.

OBJECTS OF THE INVENTION

Accordingly, it is an object of the invention to overcome the various disadvantages of the prior art processes for utilising fatty raw materials with a high free fatty acid content for the production of fatty acid esters of lower alkyl alcohols by the use of lipase enzymes.

It is another object of the invention to avoid the use of solvents.

It is also an object of the invention to use the lipase enzyme in such a way that its productivity is maximised.

It is a further object of the invention to enable the maximisation of the yield of lower alkyl esters of fatty acids based on the fatty acid moiety content of the raw material.

It is yet another object of the invention to provide a process that can accommodate a wide range of raw materials with varying free fatty acid contents.

These and further objects of the invention will become apparent from the description and the examples hereinafter.

SUMMARY OF THE INVENTION

It has surprisingly been found that there exist microbial enzymes that are effective in a solvent-free process for the production of esters of fatty acids and $C_1$-$C_3$ alkyl alcohols from a fatty material containing free fatty acids, comprising the steps of:
  (a) providing a reaction mixture that comprises free fatty acids, a lipase and one or more polyhydric alcohols;
  (b) allowing said reaction mixture to react under formation of esters of fatty acids and polyhydric alcohols until the free fatty acid content has decreased by more than a factor of 2;
  (c) separating the reaction mixture into a fatty phase and an alcoholic phase;
  (d) reducing the free fatty acid content of said fatty phase to an acid value below 2 (mg KOH per g) by subjecting it to a process of vacuum stripping or by blending it with a glyceride oil having an acid value below 2 (mg KOH per g), or by a combination of both;
  (e) transesterifying the fatty material resulting from step (d) with a $C_1$-$C_3$ alkyl alcohol.

The process of the invention saves time in comparison with the prior art by no longer aiming for an almost complete esterification of the free fatty acids with the polyhydric alcohol but instead, makes use of the productive, first part of the esterification and after partial esterification, and reduces the residual free fatty acid content by a vacuum stripping process which is preferably combined with an existing physical refining operation or by a blending process.

BRIEF DESCRIPTION OF THE DRAWING

FIG. 1 is a flow diagram illustrating several different embodiments of the invention.

DEFINITION OF TERMS

The terms to be defined below are shown in capitals and have been listed alphabetically; if a definition contains a listed term, this term has been italicised.

ACID OILS is the fatty product that results from the acidulation of soapstock. Its composition varies but it is likely to contain more than 50% by weight of free fatty acids, the remainder comprising triglyceride oil, partial glycerides and unsaponifiables.

ACIDULATION is the process used to recover the fatty matter contained in product streams comprising soaps such as soapstock. It involves adding an acid as for instance sulphuric acid, to this product stream and separating the fatty phase as acid oils from the aqueous phase.

ALCOHOLYSIS is the reaction between an alcohol and a glyceride such as an oil or fat. If the alcohol concerned is methanol, the alcoholysis can also be referred to as 'methanolysis'.

BIODIESEL is defined as esters of long chain fatty acids derived from renewable feed stocks and $C_1$-$C_3$ monohydric alcohols. Examples of such renewable feed stocks are vegetable oils and animal fats. In the context of the present invention long chain fatty acids may be defined as fatty acid chains with a length of between 10 and 22 carbon atoms.

ESTERIFICATION is the reaction between a fatty acid and an alcohol leading to an ester and water.

HYDROLYSIS is the reaction between an ester and water and is the reversible reaction of esterification.

FATTY ACID DISTILLATE is the condensate resulting from a vapour scrubbing process during the vacuum stripping of triglyceride oils which latter process is used for the physical removal of free fatty acids and for the deodorisation of triglyceride oils. In addition to FFA, the fatty acid distillate contains unsaponifiables such as but not limited to tocopherols and sterols.

FATTY FEED is a general name for raw materials containing fatty acid moieties. These can be glycerides such as monoacylglyceride, also referred to as monoglyceride, diglycerides, triglycerides and phosphatides but free fatty acids and even soaps can form part of the fatty feed.

FFA is the standard abbreviation of Free Fatty Acids.

SOAPSTOCK is the by-product of the chemical neutralisation of crude triglyceride oils. It comprises soaps, phosphatides and neutral oil besides many colouring compounds, particulate matter and other impurities as well as water containing various salts.

STRIPPING, also referred to as vacuum stripping when carried out at subatmospheric pressure, is a process that causes the most volatile constituents of a mixture to vaporise when a gas is blown through the mixture.

TRANSESTERIFICATION is another name for alcoholysis.

DETAILED DESCRIPTION OF THE INVENTION

The process of the invention provides an economic and environmentally friendly alternative to the use of the acid catalysed esterification processes that are currently used; it also causes less corrosion and produces less salt by-products. Moreover, it can accommodate raw materials with widely different FFA contents. These can be crude or degummed oils and fats of vegetable or animal origin and preferably those that have such a high FFA content that their neutralisation by conventional means is uneconomic. High acidity rice bran oil is a prime example of such oils, but palm oil may occasionally also exhibit high FFA contents. In general, oils and fats that are used for the production of soap because their FFA content is too high for economic use as food, are suitable.

Suitable raw materials for the process of the invention also comprise inedible fatty feeds such as but not limited to inedible tallow, and by-products originating from edible oil processing such as acid oils, fatty acid distillate, greases and grease trap skimmings, etc. The FFA contents of the raw materials mentioned above can vary widely. Crude rice bran oil for example can have an FFA content of more than 10% or even more than 20% or even 30%. Fatty acid distillates originating from the physical refining process can contain in excess of 90% FFA; it is an advantage of the process of the invention that it can effectively handle all these raw materials. Although the term fatty acid distillate (terms used in FIG. 1 will be written in italics from hereafter) is too narrow a description of this wide range of raw materials, this is what the term is intended to cover in FIG. 1.

FIG. 1 also shows that a non-neutral oil can be subjected to a vacuum stripping process to yield a neutral oil that has such a low FFA content that it is amenable to being transesterified with a $C_1$-$C_3$ alcohol without excessive catalyst usage, and a fatty acid distillate that is a suitable raw material for the process of the invention. Such a non-neutral oil can refer to an oil that has been degummed to a low residual phosphorus level and that is then physically refined in the process that has been indicated as vacuum stripping.

According to the process of the invention the so-called fatty acid distillate is esterified with a polyhydric alcohol which FIG. 1 refers to as glycerol. This glycerol can originate from a number of different sources. During the alcoholysis or transesterification process shown in FIG. 1, glycerol is formed as by-product of the biodiesel production. This glycerol will contain the most of the soaps formed during the alcoholysis by reaction of the alkaline catalyst with any FFA and/or water present in the feedstocks. Acidulation of this 'soapy glycerol' will convert the soaps into free fatty acids and sodium salts, the latter of which can be removed by filtration as indicated in FIG. 1. Consequently, the use of the acidulated glycerol by-product stream from the transesterification in the esterification process of the invention recuperates the fatty acid moieties converted into soaps during said transesterification and ensures they are ultimately converted into biodiesel.

Another glycerol source for the process of the invention is the alcoholic phase resulting from the process of the invention. Utilising this source is especially advantageous since it contains the lipase enzyme and thus permits this enzyme to be recycled. Consequently, it is also advantageous to wash the fatty phase resulting from the process of the invention with a polyhydric alcohol such as but not limited to glycerol, and thereby recuperate residual amounts of enzyme. The washing step has been indicated in FIG. 1, but the fact that the glycerol+FFA filtrate can be used for said washing purpose has not been shown.

In the esterification reactor, the molar ratio of hydroxyl groups in the polyhydric alcohol and the free fatty acids has to be controlled, but according to the process of the invention this ratio can vary between fairly wide limits. When glycerol is used as polyhydric alcohol, the molar ratio of glycerol to free fatty acids in the reaction mixture provided in step (a) of the process of the invention is preferably from 1:2 to 2:1. More preferably the molar ratio of glycerol to free fatty acids of the substrate feeding the enzymatic reaction is from 2:3 to 3:2. More preferably the molar ratio of glycerol to free fatty acids of the substrate feeding the enzymatic reaction is from 3:4 to 4:3. Most preferably the molar ratio of glycerol to free fatty acids of the substrate feeding the enzymatic reaction is approximately 1:1.

The biodiesel production process is a net producer of glycerol. Accordingly, the process of the invention requires a glycerol purge. In a preferred embodiment of the invention, this purge comprises a membrane filtration of the alcoholic phase that ensures that the lipase is retained, followed by the recycling of the retentate to the esterification step. The glycerol emerging as filtrate can then act as partially purified purge. The enzyme recovery and concomitant glycerol purification may be performed by any recovery method know to those skilled in the art e.g. centrifugation or membrane filtration.

The process of the invention employs a lipase enzyme as catalyst. Amongst the many microbial lipases that are now available, especially promising results have been obtained when using a carboxylic ester hydrolase (EC no 3.1.1), such as *Candida Antarctica* lipase B as the catalytic enzyme according to the invention. Normally, immobilised enzymes are preferably used in enzymatic processes, because of the reduced enzyme usage and thereby reduced costs. It has surprisingly been shown that the enzyme used in the esterification process according to the invention is effective without being immobilised and that it can be effectively isolated from the reaction mixture and recycled. By using enzymes free in solution an increased efficiency as well as increased yield may be maintained at low cost. Another benefit of not using immobilized enzyme is that the reaction media will consist of one phase less by only having a liquid fatty acid phase and a liquid glycerol phase, which need to be efficiently mixed. Consequently, in a preferred embodiment, the enzymes are liquid enzymes (i.e. enzymes that are free in solution), meaning that they are not actively immobilised on any solid support.

The amount of enzyme used is dependent upon the enzyme source and activity of the enzyme. The activity of lipases can be expressed in Lipase Units (LU) which is analyzed by measuring the amount of µmol titratable butyric acid per minute formed from tributyrin at 30° C. at pH 7. Typically, the enzyme is used in a concentration corresponding to 1 LU/g FFA to 1000 LU/g FFA. Preferably the enzyme is used in a concentration of between 5 LU/g FFA to 500 LU/g FFA, more preferably between 10 LU/g FFA to 100 LU/g FFA.

The optimum parameters for enzymatic activity will vary depending upon the enzyme used. The rate of enzyme degradation depends upon factors known in the art, including the enzyme concentration, substrate concentration, temperature, the presence or absence of inhibitors and presence of water. These parameters may be adjusted to optimise the esterification reaction.

During the enzymatic treatment step, the temperature of the suspension should be adjusted to provide effective enzyme activity. In general, a temperature of about 40° C. to about 90° C. is used, particularly from about 60° C. to about 80° C. In one embodiment the preferred temperature of the esterification reaction mixture is approx. 75° C.

During the enzymatic esterification according to the process of the invention, water is formed as a reaction product. In a preferred embodiment, this water is removed from the reaction mixture by applying a vacuum to the esterification reactor and/or by stripping its contents with an inert gas such as nitrogen or carbon dioxide. To save on the consumption of this inert gas, it can be circulated in a closed loop comprising a dryer. Superior results are obtained when a rotary jet head (EP1324818) is used to mix the stripping medium into the reaction mixture. The rotary jet head system is also providing efficient mixing of the fatty acid and the glycerol phase. To improve further the mixing of the two phases the reaction mixture can be added emulsifiers, e.g. mono-acyl glycerol and/or di-acyl glycerol. The emulsifier can be part of esterified FFA/glycerol from one batch being added to the next batch for esterification.

During the early stages of the esterification process, the rate of esterification is limited by the enzyme concentration and its activity. As and when the reaction proceeds and the concentrations of the free hydroxyl and carboxyl groups decrease, these concentrations start to become the rate limiting factors. Another factor decreasing the rate of formation of new ester bonds is the fact that the esterification reaction is reversible and leads to an equilibrium. Accordingly, in a preferred embodiment of the process of the invention, the esterification process is terminated when the productivity of the esterification (defined as the net number of ester bonds that is formed per unit of time) has fallen below a certain level, whereby the optimum of this level depends on local circumstances.

So instead of continuing the esterification process of the invention until the residual FFA content is so low that the reaction product can be transesterified without inactivating unduly high amounts of interesterification catalyst, a preferred embodiment of the invention halts the interesterification step (b) of the process of the invention when the FFA content of the reaction mixture has decreased by a factor of more than 2. If the FFA content of the reaction mixture provided in step (a) of the process of the invention is high and for instance more than 50%, the esterification can be profitably continued until the FFA content of the reaction mixture has decrease by a factor of more than 4 or even more than 8.

Consequently, the FFA content of the reaction mixture is likely to be too high for profitable transesterification leading to biodiesel, when the esterification process of the invention is halted. Instead and as illustrated in FIG. 1, a fatty phase is isolated from the esterification reaction mixture and this fatty phase is then either subjected to a vacuum stripping treatment to reduce its FFA content or mixed with neutral oil to provide a blend with an FFA content below 1%, which is amenable to profitable transesterification and biodiesel production. These operations: vacuum stripping and blending, are additional treatments and thereby add to the cost of the process as a whole but if a vacuum stripping process is being operated on site anyway, processing a bit more involves only marginal costs, and blending is one of the cheapest if not the cheapest process being operated in the sector concerned.

Given the low price of blending, a preferred embodiment of the process of the invention comprises lowering the FFA content of the esterification reaction mixture to a value of 2 to 10% by vacuum stripping and subsequently lowering it further to 1% or lower by blending with neutralised oil. This has the advantage that only a small amount of monoglycerides will be lost during vacuum stripping and thus improves the biodiesel yield of the process of the invention. When the esterification mixture is mixed with high FFA oil to be vacuum stripped, no separate subsequent blending step is required.

Example 1

In this example, a palm oil fatty acid distillate with an FFA content of 90% was mixed with pure glycerol in a molar ratio of 1:1. The mixture was introduced into a stirred reactor held at a pressure of 5 mbar absolute, and kept at 68° C. CALB L lipase (liquid enzyme from *Candida Antartica* lipase B supplied by Novozymes A/S Denmark) was added in a concentration of 175 LU per g FFA. After 8 hours reaction, the FFA content had been reduced to 7% due to the formation of mono-, di- and triacylglycerides.

This example shows that the liquid enzyme from *Candida Antartica* is capable of reducing high levels of FFA within a reasonable period of time.

Example 2

In this example, the effect of the esterification temperature was investigated. The same palm oil fatty distillate and the same enzyme preparation were used as in example 1 and the FFA to glycerol ratio was again 1:1, but the enzyme dosage was only 100 LU per g FFA. After 8 hours reaction, the FFA content of the reaction carried out at 75° C. had dropped to 9% whereas when the reaction was carried out at the lower temperature of 58° c., the residual FFA content was higher at 15%. The experiment shows that operating at the higher of the two temperatures led to a larger extent of FFA esterification but the example does not indicate whether this difference is due to differences in enzyme activity or in water volatility.

Example 3

In this example, another lipase was tested. The same palm oil fatty distillate as used in example 1 was used and the FFA to glycerol ratio was again 1:1. The enzyme tested was Lipozyme TL IM, an immobilised enzyme from *Thermomyces lanuginosus* supplied by Novozyme A/S, Denmark; it was used in an amount of 4% by weight on oil. The reaction temperature was 68° C. and the reactor was kept at 5 mbar absolute. After 6 hours the FFA content of the reaction mixture had fallen to 79%.

This experiment shows that Lipozyme TL IM is not a suitable enzyme for the process of the invention.

Example 4

In this example, the effect of reaction time on conversion will be shown. A rapeseed oil fatty distillate with an FA content of 46% was mixed with glycerol in a molar ratio of glycerol to FFA of 1:1 and an amount of CALB L that was also used in example 1 was added in an amount of 175 LU per g oil FFA. The reaction temperature was 68° C. and the pressure inside the reactor was 5 mbar absolute. A sample take after 4 hours of reaction had an FFA content of 13% and after 8 hours of reaction it still contained 5% FFA.

This example shows that the esterification is quite rapid at the beginning, when the FFA content is still high but slows down considerably when the FFA content has dropped. This means that it can be advantageous to terminate the reaction well before such a low FFA content has been reached that blending with neutralised oil will bring this FFA content below a value that permits profitable transesterification. In general, the most profitable embodiment of the process of the invention comprises an esterification of the FFA in the fatty acid distillate to a residual FFA content of for instance about 10%, mixing with high FFA oil and vacuum stripping of the resulting mixture to yield a neutral oil that can be profitably interesterified. This embodiment combines: the high productivity first stage of the esterification step with vacuum stripping conditions that avoid the loss of monoglycerides.

Example 5

This example illustrates the beneficial effect of stripping the reaction mixture in step (b). The reaction mixture consisting of glycerol and oleic acid in ratio 33:77 w/w % was flushed with nitrogen during reaction at atmospheric pressure. *C. antartica* B liquid was used in dosage of 50 LU/g FFA and temperature 70° C. Sampling after 2 hours, 4 hours and 21 hours showed following conversions: 6%, 32%, and 89%, respectively.

Example 6

From 1000 Kg Palm oil with 5% FFA is obtained approximately 945 Kg FFA-low oil with low FFA content and approximately 55 Kg with high FFA (approx. 90%) content. After the reaction the FFA content of is reduced to e.g. 8% (as shown in example 1). Adding this directly back to the FFA-low oil will result in 1000 Kg of oil containing 4 Kg FFA equals 0.4% FFA in the product going to methanolysis, which fulfil the specifications for oil raw material for the methanolysis process, i.e. below 0.5%.

The invention claimed is:

1. A process for the production of esters of fatty acids and C1-C3 alkyl alcohols from a fatty material containing free fatty acids, comprising the steps of:
   (a) providing a reaction mixture that comprises free fatty acids, a lipase and one or more polyhydric alcohols;
   (b) allowing said reaction mixture to react under formation of esters of fatty acids and polyhydric alcohols until the free fatty acid content has decreased by more than a factor of 2;
   (c) separating the reaction mixture into a fatty phase and an alcoholic phase;
   (d) reducing the free fatty acid content of said fatty phase to an acid value below 2 (mg KOH per g) by subjecting it to a process of vacuum stripping or by blending it with a glyceride oil having an acid value below 2 (mg KOH per g) or by a combination of both;
   (e) transesterifying the fatty material resulting from step (d) with a C1-C3 alkyl alcohol.

2. The process according to claim 1 in which the polyhydric alcohol is glycerol.

3. The process according to claim 1 in which the lipase is a liquid.

4. The process according to claim 1 in which the lipase is a microbial lipase.

5. The process according to claim 1 in which the lipase is *Candida Antarctica* type B lipase.

6. The process according to claim 1 in which emulsifiers are added to the reaction mixture in step (a).

7. The process according to claim 1 in which the emulsifiers are mono-acyl glycerol and/or di-acyl glycerol.

8. The process according to claim 1 in which the lipase is recuperated from the alcohol phase arising in step (c) by a process of membrane filtration.

9. The process according to claim 1 in which the lipase is recuperated from the alcoholic phase arising in step (c) by a process of centrifugation.

10. The process according to claim 1 in which the lipase is re-used by recycling the alcoholic phase arising in step (c) to step (a).

11. The process according to claim 1 in which the temperature of the reaction mixture in step (b) is kept between 40 and 90° C.

12. The process according to claim 1 in which the temperature of the reaction mixture in step (b) is kept between 60 and 80° C.

13. The process according to claim 1 in which a vacuum is applied to the reaction mixture while it reacts in step (b).

14. The process according to claim 1 in which the reaction mixture is subjected to a stripping treatment by passing a stream of inert gas through said mixture while it reacts in step (b).

15. The process according to claim 14 in which the inert stripping gas is dispersed in the reaction mixture by means of a rotary jet head.

16. The process according to claim 14 in which the stripping gas is contained in a closed loop comprising an air dryer.

* * * * *